United States Patent
Beardsley

[19]

[11] Patent Number: 6,154,559

[45] Date of Patent: Nov. 28, 2000

[54] SYSTEM FOR CLASSIFYING AN INDIVIDUAL'S GAZE DIRECTION

[75] Inventor: Paul Anthony Beardsley, Boston, Mass.

[73] Assignee: Mitsubishi Electric Information Technology Center America, Inc. (ITA), Cambridge, Mass.

[21] Appl. No.: 09/164,734

[22] Filed: Oct. 1, 1998

[51] Int. Cl.[7] ..................................................... G06K 9/00

[52] U.S. Cl. ........................ 382/103; 382/104; 382/170; 340/576

[58] Field of Search ................................... 382/103, 117, 382/118, 100, 159, 104, 168, 170; 345/7, 8, 326, 146, 327; 340/907, 908, 576, 575, 573.1; 348/113, 77, 78, 118, 169, 172

[56] References Cited

U.S. PATENT DOCUMENTS

| | | | |
|---|---|---|---|
| 3,805,238 | 4/1974 | Rothfjell | 340/146.3 |
| 5,008,946 | 4/1991 | Ando | 382/104 |
| 5,293,427 | 3/1994 | Ueno et al. | 382/103 |
| 5,454,043 | 9/1995 | Freeman | 382/168 |
| 5,481,622 | 1/1996 | Gerhardt et al. | 382/103 |
| 5,886,683 | 3/1999 | Tognazzini et al. | 345/146 |
| 6,009,210 | 12/1999 | Kang | 382/276 |
| 6,061,055 | 5/2000 | Marks | 345/327 |

FOREIGN PATENT DOCUMENTS

| | | | |
|---|---|---|---|
| 0 305 124 | 3/1989 | European Pat. Off. | G09B 5/06 |
| WO/90/02453 | 3/1990 | WIPO | H04H 9/00 |

*Primary Examiner*—Joseph Mancuso
*Assistant Examiner*—Vikkram Bali
*Attorney, Agent, or Firm*—Dirk Brinkman

[57] ABSTRACT

A system is provided to classify the gaze direction of an individual observing a number of surrounding objects. The system utilizes a qualitative approach in which frequently occurring head poses of the individual are automatically identified and labelled according to their association with the surrounding objects. In conjunction with processing of eye pose, this enables the classification of gaze direction. In one embodiment, each observed head pose of the individual is automatically associated with a bin in a "pose-space histogram". This histogram records the frequency of different head poses over an extended period of time. Given observations of a car driver, for example, the pose-space histogram develops peaks over time corresponding to the frequently viewed directions of toward the dashboard, toward the mirrors, toward the side window, and straight-ahead. Each peak is labelled using a qualitative description of the environment around the individual, such as the approximate relative directions of dashboard, mirrors, side window, and straight-ahead in the car example. The labelled histogram is then used to classify the head pose of the individual in all subsequent images. This head pose processing is augmented with eye pose processing, enabling the system to rapidly classify gaze direction without accurate a priori information about the calibration of the camera utilized to view the individual, without accurate a priori 3D measurements of the geometry of the environment around the individual, and without any need to compute accurate 3D metric measurements of the individual's location, head pose or eye direction at run-time.

9 Claims, 11 Drawing Sheets

(a) Initialize 3D model

(b) Generate templates (c) Match image with template (d) Compute eye pose (e) Record head pose in pose-space histogram

FIG. 4

FIG. 5 target image residuals across pose-space
looking left      looking right

SYSTEM FOR CLASSIFYING AN INDIVIDUAL'S GAZE DIRECTION

FIELD OF INVENTION

This invention relates to the classification of gaze direction for an individual, and more particularly to a qualitative approach which involves automatic identification and labeling of frequently occurring head poses by means of a pose-space histogram, without any need for accurate camera calibration or explicit 3D metric measurements of the surrounding environment, or of the individual's head and eyes.

BACKGROUND OF THE INVENTION

In the past, the classification of the gaze direction of a vehicle driver has been important to determine, amongst other things, a drowsy driver. Moreover gaze detection systems, in conjunction with external sensors such as infrared, microwave or sonar ranging to ascertain obstacles in the path of the vehicle, are useful to determine if a driver is paying attention to possible collisions. If the driver is not paying attention and is rather looking away from the direction of travel, it is desirable to provide an alarm of an automatic nature. Such automatic systems are described in "Sounds and scents to jolt noisy drivers", Wall Street Journal, page B1, May 3, 1993. Furthermore, more sophisticated systems might attempt to learn the characteristic activity of a particular driver prior to maneuvers, enabling anticipation of those maneuvers in the future.

An explicit quantitative approach to this problem involves (a) calibrating the camera used to observe the driver, modeling the interior geometry of the car, and storing this as a priori information, and (b) making an accurate 3D metric computation of the driver's location, head pose and gaze direction. Generating a 3D ray for the driver's gaze direction in the car coordinate frame then determines what the driver is looking at.

There are problems with this approach. Firstly, although the geometry of the car's interior will usually be known from the manufacturer's design data, the camera's intrinsic parameters, such as focal length, and extrinsic parameters, such as location and orientation relative to the car coordinate frame, need to be calibrated. That extrinsic calibration may change over time due to vibration. Furthermore, the location of the driver's head, head pose and eye direction must be computed in the car coordinate frame at run-time. This is difficult to do robustly, and is intensive for the typical low-power processor installed in a car.

SUMMARY OF INVENTION

Acknowledging these difficulties, an alternative approach is adopted which avoids altogether the need for accurate camera calibration, accurate 3D measurements of the geometry of the surrounding environment, or 3D metric measurements of driver location, head and eye pose. The term "qualitative" as used herein indicates that there is no computation of 3D metric measurements, such as distances and angles for the individual's head. In the subject system, the measurements carried out are accurate and repeatable and fulfill the required purpose of classifying gaze direction.

In one embodiment, each possible head pose of the individual is associated with a bin in a "pose-space histogram". Typically the set of all possible head poses, arising from turning the head left to right, up and down, and tilting sideways, maps to a few hundred different bins in the histogram. A method is provided below for efficiently matching an observed head pose of the driver to its corresponding histogram bin, without explicit 3D metric measurements of the individual's location and head pose. Each time an observed head pose is matched to a histogram bin, the count in that bin is incremented. Over an extended period of time, the histogram develops peaks which indicate those head poses which are occurring most frequently. For a car driver, peaks can be expected to occur for the driver looking toward the dashboard, at the mirrors, out of the side window, or straight-ahead. It is straightforward to label these peaks from a qualitative description of the relative location of dashboard, mirrors, side window and windscreen. The gaze direction of the driver in all subsequent images is then classified by measuring head pose and checking whether it is close to a labelled peak in the pose-space. The basic scheme is augmented, when necessary, by processing of eye pose as described further below.

In one embodiment, there are five components to the system—(a) initialization, (b) a fast and efficient method for associating an observed head pose with a number of possible candidate "templates", which are synthetically generated images showing various poses of the head, followed by (c) a refinement method which associates the observed head pose with a unique template, (d) augmentation of the head pose processing with eye pose processing if necessary, and (e) classification of the gaze direction.

Initialization employs a generic head model to model the individual's head. A generic head model, as used herein, refers to a digital 3D model in the computer database with the dimensions of an average person's head. For the initialization phase, the camera is trained on the individual as the head is moved during a typical driving scenario. The subject system automatically records the texture or visual appearance of the individual's face, such as skin color, hair color, the appearance of the eyebrows, eyes, nose, and ears, and the appearance of glasses, a beard or a moustache. The texture is used in conjunction with the generic head model to generate an array of typically several hundred synthetic templates which show the appearance of the individual's head over a range of all the head poses which might occur. The synthetic templates include head poses which were not seen in the original images. Corresponding to each template in the template array, there is a bin in the pose-space histogram. All bins in the histogram are initialized to zero.

Four main pieces of information are computed and stored for each template. Firstly, the position of the eyes on the generic head model is known a priori, hence the position of the eye or eyes is known in each template. Secondly, the skin region in the templates is segmented, or identified, using the algorithm in "Finding skin in color images" by R. Kjeldsen et al, 2nd Intl Conf on Automatic Face and Gesture Recognition, 1996. Thirdly, a 1D projection is taken along the horizontal direction of each template, with this projection containing a count of the number of segmented skin pixels along each row. Fourthly, moments of the skin region are computed to provide a "shape signature" for the skin region. Examples of moments are described in "Visual Pattern Recognition by Moment Invariants" by M. K. Hu, IEEE Trans Inf Theory, IT-8, 1962. For clarity below, the segmented skin region of a template will be referred to as TS, and the 1D projection will be referred to as T1D.

As to fast matching of observed head pose to several possible candidate templates, a newly acquired image of an individual is processed by segmenting the skin region, and creating a 1D projection of the segmented region along the horizontal direction. The segmented region is labeled RS and the 1D projection is labelled R1D.

The first part of the processing deals with the problem that the segmented region RS may be displaced from the image center. Furthermore, region RS contains the head and may also contain the neck, but the segmented skin region TS in a template contains the individual's head only and not the neck. In order to do a comparison between RS and TS, the position of the face must be localized and the neck part must be discarded from the comparison.

Consider the comparison between the acquired image and one specific template. The horizontal offset between the center of gravit3, COG, of the region RS and the COG of the region TS is taken as the horizontal offset which is most likely to align the face in the image and template.

Then 1D projection R1D for the acquired image is compared with the 1D projection T1D for the template using the comparison method in "Color Constant Color Indexing" by B. V. Funt and G. D. Fillayson, PAMI, Vol 17, No 5, 1995, for a range of offsets between R1D and T1D. The offset at which R1D is most similar to T1D indicates the vertical offset between the acquired image and the template which is most likely to align the face in the acquired image and template. Thus the face has now also been localized in the vertical direction and the remaining processing will be carried out in such a way that the individual's neck, if present, is disregarded.

With the acquired image aligned with the template using the computed horizontal and vertical offsets, the moments of the parts of skin region RS in the acquired image which overlap the skin region TS in the template are computed. A score, labelled S, is computed for the measure of similarity between the moments for region RS and the moments for region TS. This process is repeated for every template to generate a set of scores $S_1, S_2, \ldots S_n$. The templates are ranked according to score and a fixed percentage of the top-scoring templates is retained. The remaining templates are discarded for the remainder of the processing on the current image.

As to matching of observed head pose to a unique template, the previous section described the use of segmented skin regions and their shape, based on moments, to identify the most likely matching templates. Processing now returns to the raw color pixel data, including all pixels, skin and non-skin.

Consider the comparison between the acquired image and one specific template from the set of surviving candidates. The position of the face in the acquired image which is most consistent with the face in the template has already been determined, as described in the localization process above. At this position, the acquired image is compared with the synthetic template using cross-correlation of the gradients of the image color, or "image color gradients". This generates a score for the similarity between the individual's head in the acquired image and the synthetic head in the template.

This is repeated for all the candidate templates, and the best score indicates the best-matching template. The histogram bin corresponding to this template is incremented. It will be appreciated that in the subject system, the updating of the histogram, which will subsequently provide information about frequently occurring head poses, has been achieved without making any 3D metric measurements such as distances or angles for the head location or head pose.

Note that the cross-correlation used in this stage is computationally intensive making it difficult to achieve real-time processing when comparing an image with hundreds of templates. By first carrying out the fast culling process described previously to eliminate templates which are unlikely to match, cross-correlation can be incorporated at this stage while still achieving real-time processing.

As to processing of eye pose, head pose alone does not always determine gaze direction. But for the illustrative application here, the head pose is often a good indicator of the driver's focus of attention. For instance, looking at the side or rear-view mirrors always seems to involve the adoption of a particular head pose. The situation is different when one wishes to discriminate between a driver looking straight-ahead or looking towards the dashboard, since this may involve little or no head motion. To deal with the latter case, the subject system further utilizes a qualitative classification of eye direction to indicate whether the eyes are directed straight-ahead or downward. This processing is only applied if necessary. For the illustrative application, it is only applied if the driver's head pose is straight-ahead in which case it is necessary to discriminate between eyes straight-forward and eyes downward.

At this stage, the acquired image has been matched to one of the templates, and since the position of the eye or eyes in this template is known, the position of the eyes in the acquired image is also known. The algorithm for processing the eyes is targetted at the area around their expected position and not over the whole image.

Skin pixels have already been identified in the acquired, image. In the area around the eye, the skin segmentation is examined. Typically, for an individual without glasses, the segmented skin region will have two "holes" corresponding to non-skin area, one for the eyebrow and one for the eye, and the lower of these two holes is taken. This hole has the same shape as the outline of the eye. The "equivalent rectangle" of this shape is computed. An algorithm to do this is described in "Computer Vision for Interactive Computer Games" by Freeman et al, IEEE Computer Graphics and Applications, Vol 18, No 3, 1998. The ratio of the height of this rectangle to its width provides a measure of whether the eye is directed straight-forward or downward. This is because looking downward causes the eyelid to drop, hence narrowing the outline of the eye, and causing the height of the equivalent rectangle to decrease. A fixed threshold is applied to the height/width ratio to decide if the eye is directed straight-forward or downward.

As to classification of the gaze direction, the time history of the observed head behavior is recorded in the pose-space histogram in the following way. As already described, each time an image is matched to its most similar template, the element in the histogram corresponding to that template is incremented. Note, in one embodiment, there is one histogram element corresponding to each template. Peaks will appear in the histogram for the most frequently adopted head poses, and hence for the most frequently recurring view directions. Each peak is labelled using qualitative or approximate information about the geometry of the vehicle around the driver.

The gaze direction of the driver in any subsequent image is classified by matching that image with a template, finding the corresponding element in the histogram, and checking for a nearby labelled peak. In some cases, this must be augmented with information about the eye pose e.g. in the illustrative car driver application, if the driver's head pose is straight-ahead, the eye pose is processed to determine if the driver is looking straight-forward or downward.

To enhance the basis scheme to distinguish between roving motions of the gaze and fixations of the gaze, the duration that the individual holds a particular head pose is taken into account before updating the pose-space histogram.

Thus, it is possible without accurate a priori knowledge about camera calibration or accurate measurements of the environment, and without metric measurements of the head and eyes, to classify gaze direction in real-time. In the automotive alarm application, this permits the generation of appropriate alarms or cues. While the subject system is described in terms of an automotive alarm application, other applications such as time-and-motion studies, observing hospital patients, and determining activity in front of a computer monitor are within the scope of this invention. The algorithms used are appropriate for the Artificial Retina (AR) camera from Mitsubishi Electric Corporation, as described in "Letters to Nature", Kyuma et al, Nature, Vol 372, p. 197, 1994.

In summary, a system is provided to classify the gaze direction of an individual observing a number of surrounding objects. The system utilizes a qualitative approach in which frequently occurring head poses of the individual are automatically identified and labelled according to, their association with the surrounding objects. In conjunction with processing of eye pose, this enables the classification of gaze direction.

In one embodiment, each observed head pose of the individual is automatically associated with a bin in a "pose-space histogram". This histogram records the frequency of different head poses over an extended period of time. Given observations of a car driver, for example, the pose-space histogram develops peaks over time corresponding to the frequently viewed directions of toward the dashboard, toward the mirrors, toward the side window, and straight-ahead. Each peak is labelled using a qualitative description of the environment around the individual, such as the approximate relative directions of dashboard, mirrors, side window, and straight-ahead in the car example. The labelled histogram is then used to classify the head pose of the individual in all subsequent images. This head pose processing is augmented with eye pose processing, enabling the system to rapidly classify gaze direction without accurate a priori information about the calibration of the camera utilized to view the individual, without accurate a priori 3D measurements of the geometry of the environment around the individual, and without any need to compute accurate 3D metric measurements of the individual's location, head pose or eye direction at run-time.

BRIEF DESCRIPTION OF THE DRAWINGS

These and other features of the subject invention will be better understood with respect to the Detailed Description taken in conjunction with the Drawings, of which:

FIGS. 12A–B are a series of images showing how dropping of the eyelid narrows the segmented area so that, by means of the equivalent rectangle as illustrated in FIG. 11, it is possible to classify eye direction as straight-forward or downward.

DETAILED DESCRIPTION

Figure 1A:
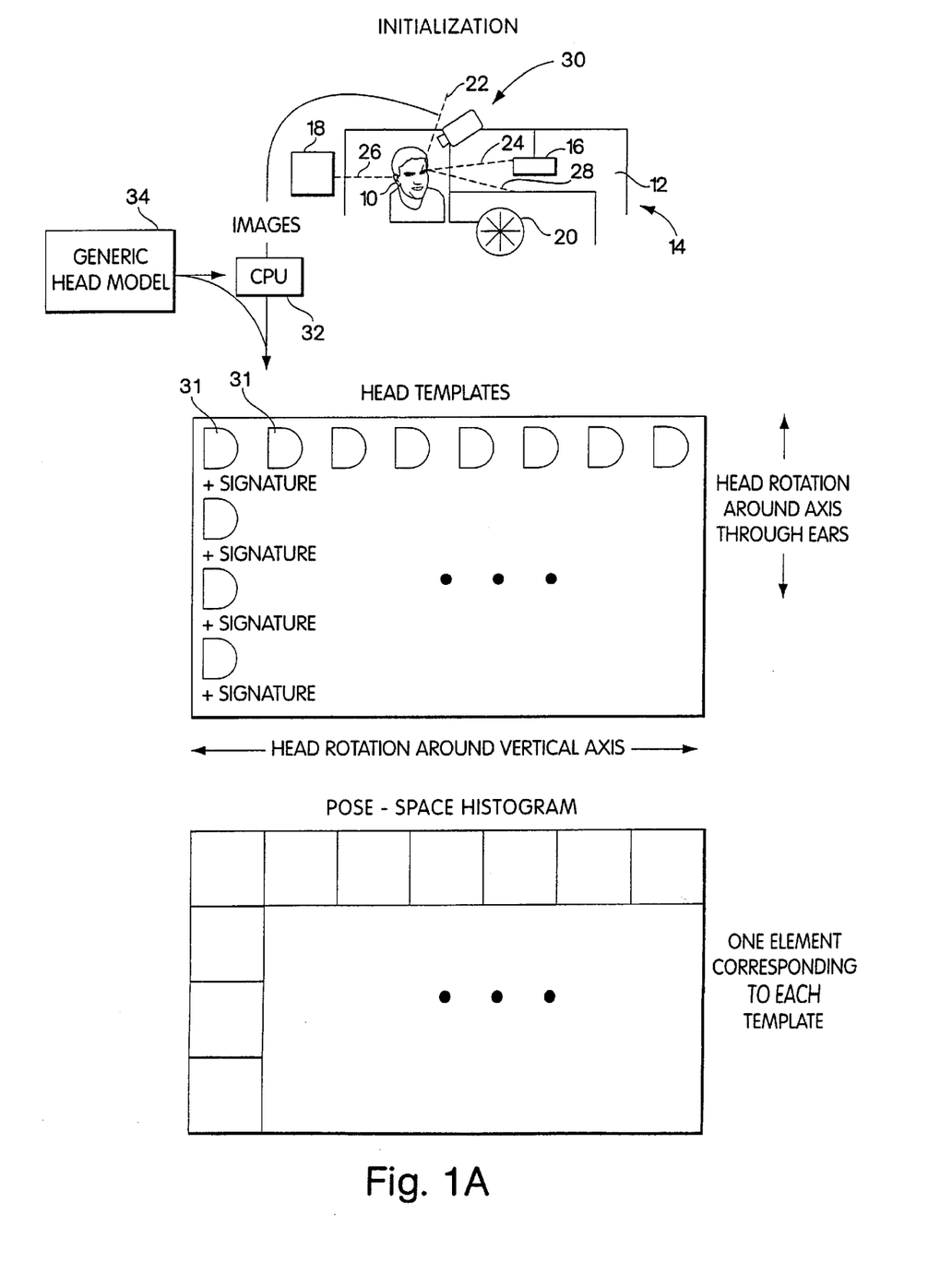
FIG. 1A is a diagrammatic representation of the initialization stage for the subject system in which head templates and pose-space histograms are generated, with each head template having associated "shape signature" information, and with the shape signature consisting of (a) a region of the template which has been segmented, or identified, as skin, (b) a 1D projection along the horizontal direction, which gives the number of segmented skin pixels along each row of the template, and (c) a set of moments for the segmented skin region.

Referring now to FIG. 1A, an individual 10 is shown seated in front of a windshield 12 of a car 14 having a mirror 16 at the center of the windshield and a side mirror 18 as illustrated. Also illustrated is an instrument cluster 20 with the individual either staring straight-ahead as indicated by dotted line 22, toward mirror 16 as illustrated by dotted line 24, towards side mirror 18 as illustrated by dotted line 26, or toward the instrument cluster as illustrated by dotted line 28.

A camera 30 is trained on the individual 10 and supplies images to a CPU 32 which is coupled to a computer database containing a digital generic head model 34. The processing by CPU 32 provides a number of templates, here illustrated at 31, each a synthetically generated image showing showing the appearance of the individual's head for a specific head pose. The templates are generated through the operation of the generic head model in concert with the texture obtained from the images of the individual. In one embodiment, a number of shape signatures, such as segmented skin region together with 1D projections and moments of the region, are used to characterize the skin region of the template to permit rapid matching. A pose-space histogram is initialized with one element corresponding to each template, and all elements initialized to zero.

Figure 1B:
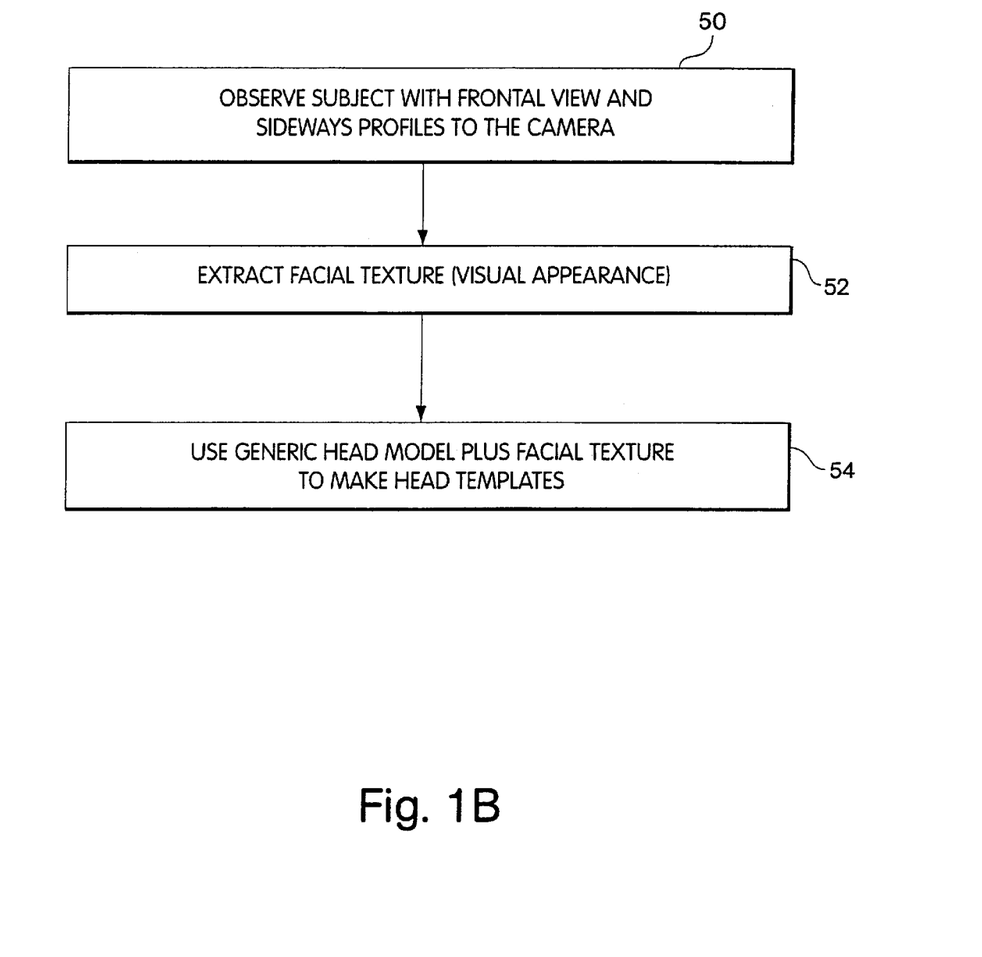
FIG. 1B is a flow chart illustrating how head templates are made.

Referring now to FIG. 1B, the steps utilized to generate the templates are illustrated. Here as a first step, camera 30 observes the individual as the individual adopts fronto-parallel and sideways-facing views relative to the camera. The term "fronto-parallel" is used herein to mean that the face is directed straight into the camera. Facial texture in terms of visual appearance is extracted in a conventional manner. Thereafter, as illustrated in 54, the facial texture is used along with the generic head model to generate the templates for a wide range of possible orientations of the head.

Figure 2A:
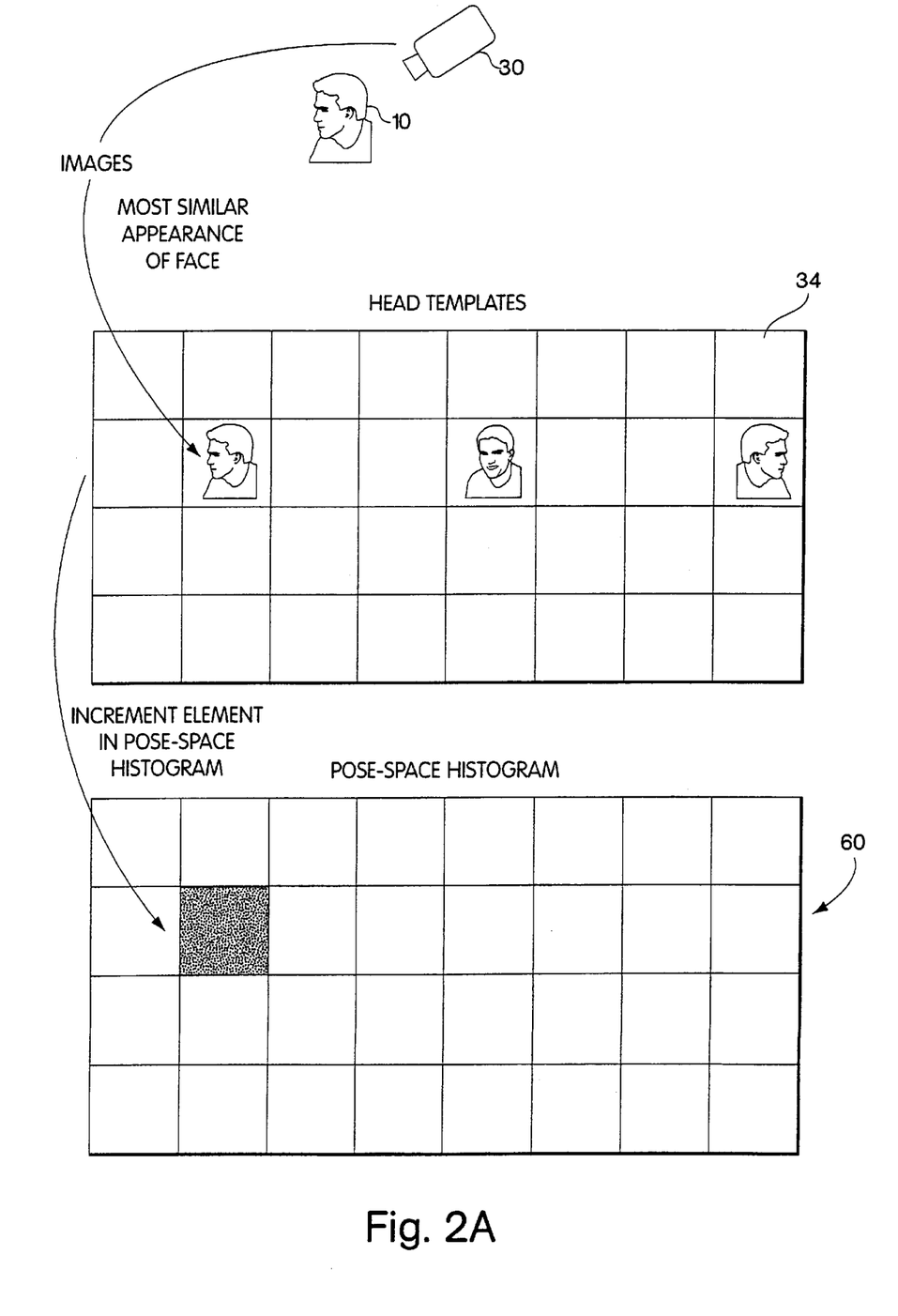
FIG. 2A is a diagrammatic representation of the run-time processing for matching an acquired image to a template, and incrementing the corresponding element in the pose-space histogram.

Referring now to FIG. 2A, camera 30 is utilized to capture an image of the individual, with CPU 32 determining which of the templates 34 is most similar in appearance to that of the face of individual 10 as recorded by camera 30.

Figure 2B:
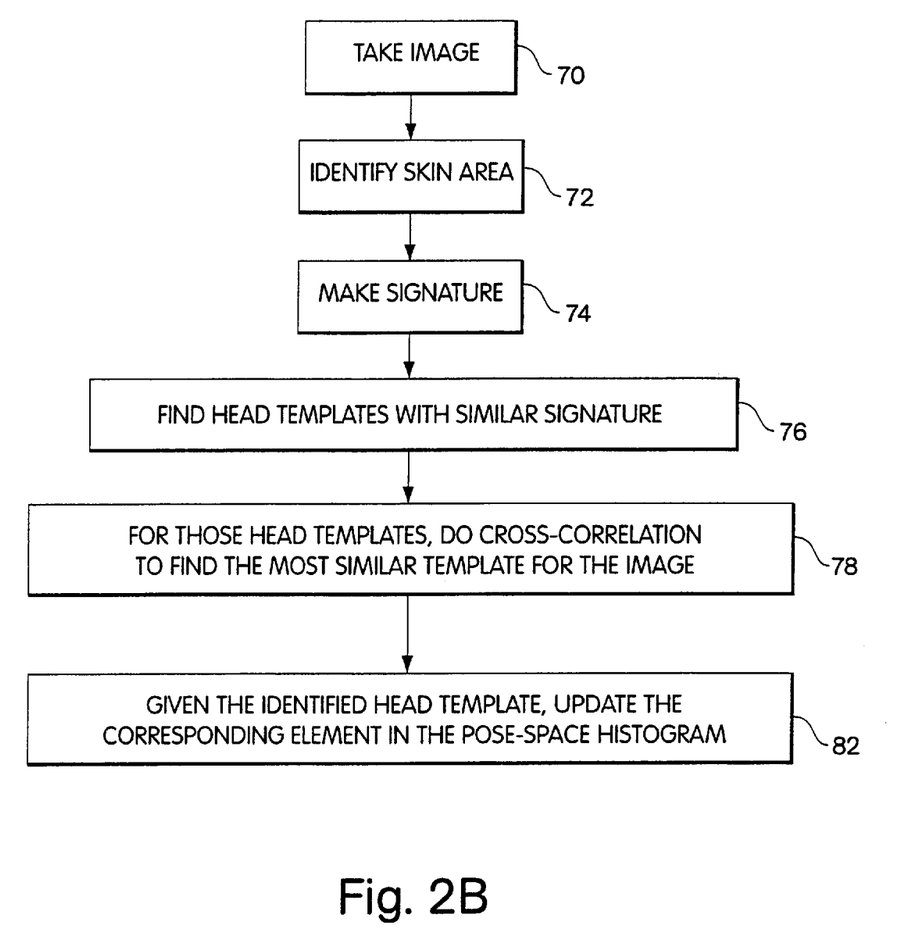
FIG. 2B is a flow chart illustrating the steps for identifying the appropriate head template given an input image and updating the corresponding element in the pose-space histogram of FIG. 2A.

Referring now to FIG. 2B, a series of steps is performed when matching an image to its most similar template. Here, as illustrated at 70, one takes the image at camera 30 and as illustrated at 72 identifies the skin area. The reason that this is done is to be able to detect the form of the face which is easily recognizable, without having to consider non-skin areas such as the eyeball, teeth, and hair. Thereafter, as illustrated at 74, a signature is generated for this skin area. The signature in one embodiment is a compact representation of the shape of the skin area, which makes possible rapid matching of the image from camera 30 to the templates.

As illustrated at 76, templates with similar signatures are found in a matching process in which the shape signature of the image is compared with the shape signature of each template, and similar signatures are identified. As illustrated at 78, for these similar templates, a cross-correlation of image color gradients is performed between the image and each template to find the most similar template. Having ascertained the template which most closely corresponds, the corresponding bin in the pose-space histogram 60 is incremented as illustrated at 82.

Figure 3A:
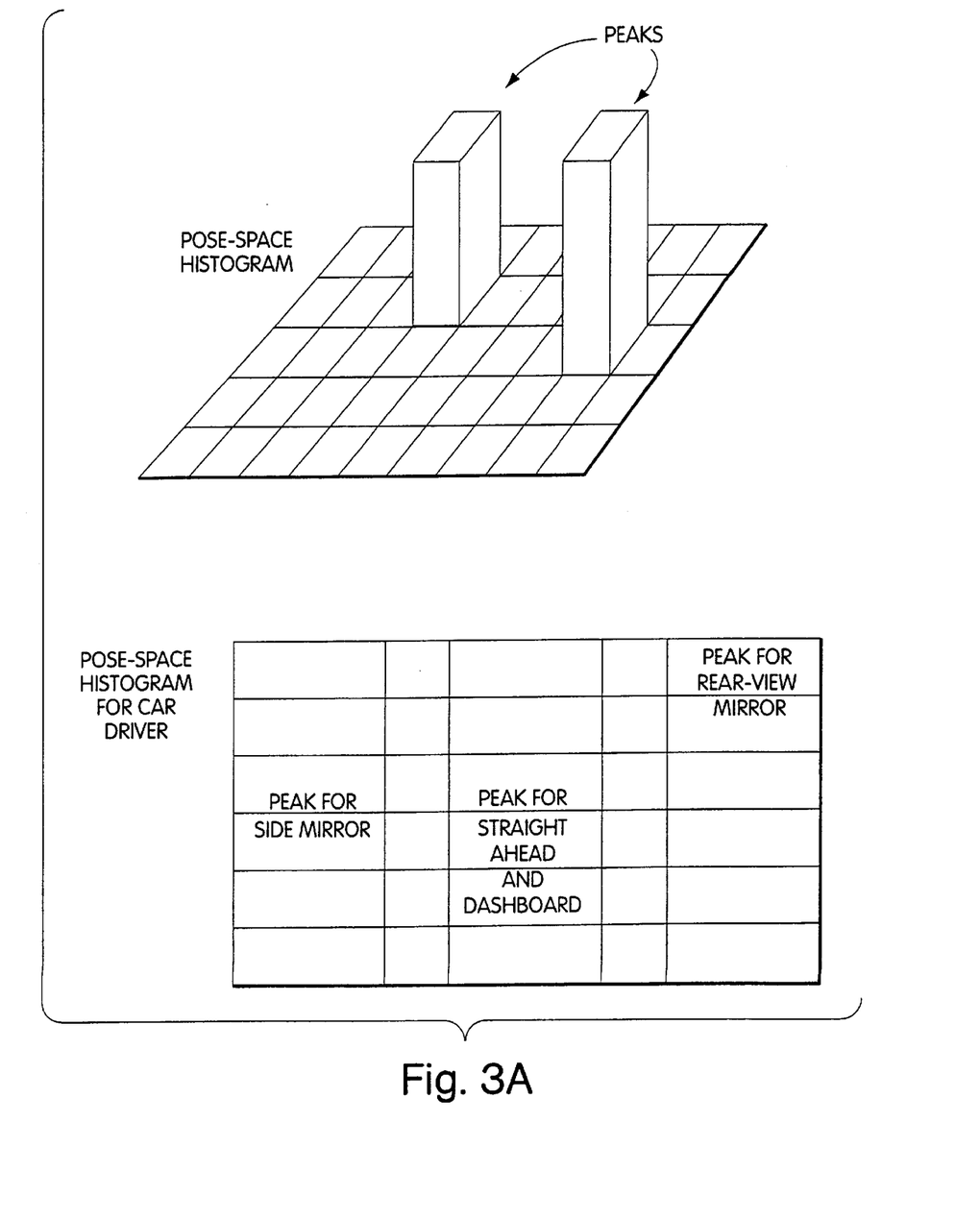
FIG. 3A is a diagrammatic representation of the gaze classification, which takes place after the system has been running for a short duration, in which peaks in the pose-space histogram are labelled according to their association with objects of interest in the surrounding environment, with any subsequent image thereafter being classified by matching to a template, finding the corresponding element in the pose-space histogram and checking for a nearby labelled peak.

Referring now to FIG. 3A, after the system has been running for a short duration to allow the development of peaks corresponding to frequent gaze directions in the pose-space histogram, these peaks are automatically detected and labelled according to their association with objects of interest in the surrounding environment. In the illustrative car driver application, the peaks correspond to viewing the the dashboard, the mirrors, or straight-ahead.

Figure 3B:
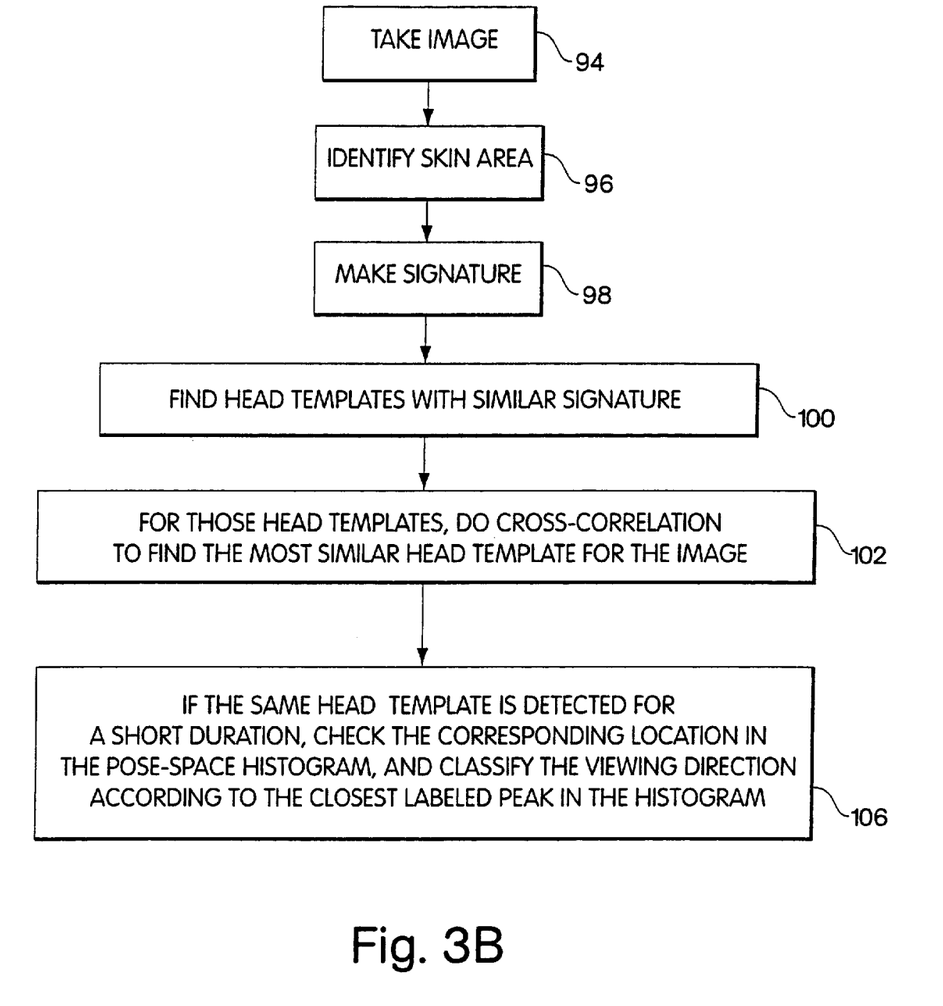
FIG. 3B is a flow chart illustrating the checking of the location in the pose-space histogram for the occurrence of the same head template over a short period of time to classify gaze direction.

Referring now to FIG. 3B, gaze classification takes place by processing an acquired image of the individual in the same way as in FIG. 2B, but as a final step, and as illustrated at 106, if the same head template is matched for a short duration, the subject system checks the corresponding location in the pose-space histogram, and the viewing direction is classified according to the closest labelled peak in the histogram. The result is a determination that the individual is looking in a direction corresponding to a direction in which he frequently gazes. Thus, without actual 3D metric measurements, such as distance and angle, of head position or eye position, one can ascertain the gaze direction without having to know anything about either the individual or his environment.

Figure 3C:
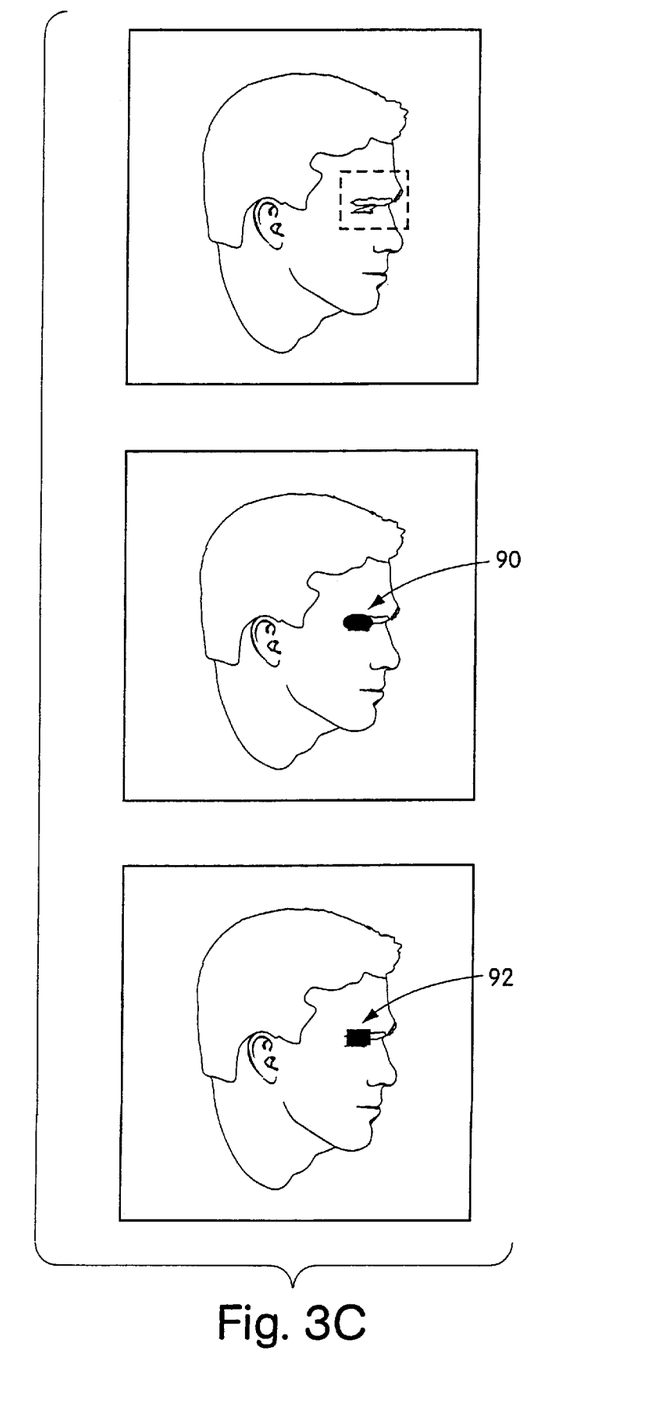
FIG. 3C is a series of illustrations showing eye segmentation, or identification, and generation of an equivalent rectangle which is used to identify the eye direction, straight-forward or down.

Referring now to FIG. 3C, some head poses are not sufficient on their own to classify the gaze direction. In this case, extra processing is carried out on the eye direction. The segmented eye 90 in the acquired image is examined and fitted with an equivalent rectangle 92 which gives a measure of whether the eye is directed straight-forward or downward. In the illustrative car driver application, If the head pose is straight-ahead, the eye pose is examined. if the eye pose is also straight-ahead, the gaze is classified as straight-ahead. If the eye pose is downward, the gaze is classified as toward the dashboard.

In one embodiment of the subject invention, the characterization of a face is accomplished using an ellipsoid such as described by Basu, Essa, and Pentland in a paper entitled "Motion Regularization for Model-Based Head Tracking", 13th Int Conf on Pattern recognition, Vienna 1996. In another embodiment, the subject invention characterizes the face using the aforementioned generic head model as described in "Human Face Recognition: From Views to Models—From Models to Views", Bichsel, 2nd Intl Conf on Face and Gesture Recognition, 1996.

Figure 4:
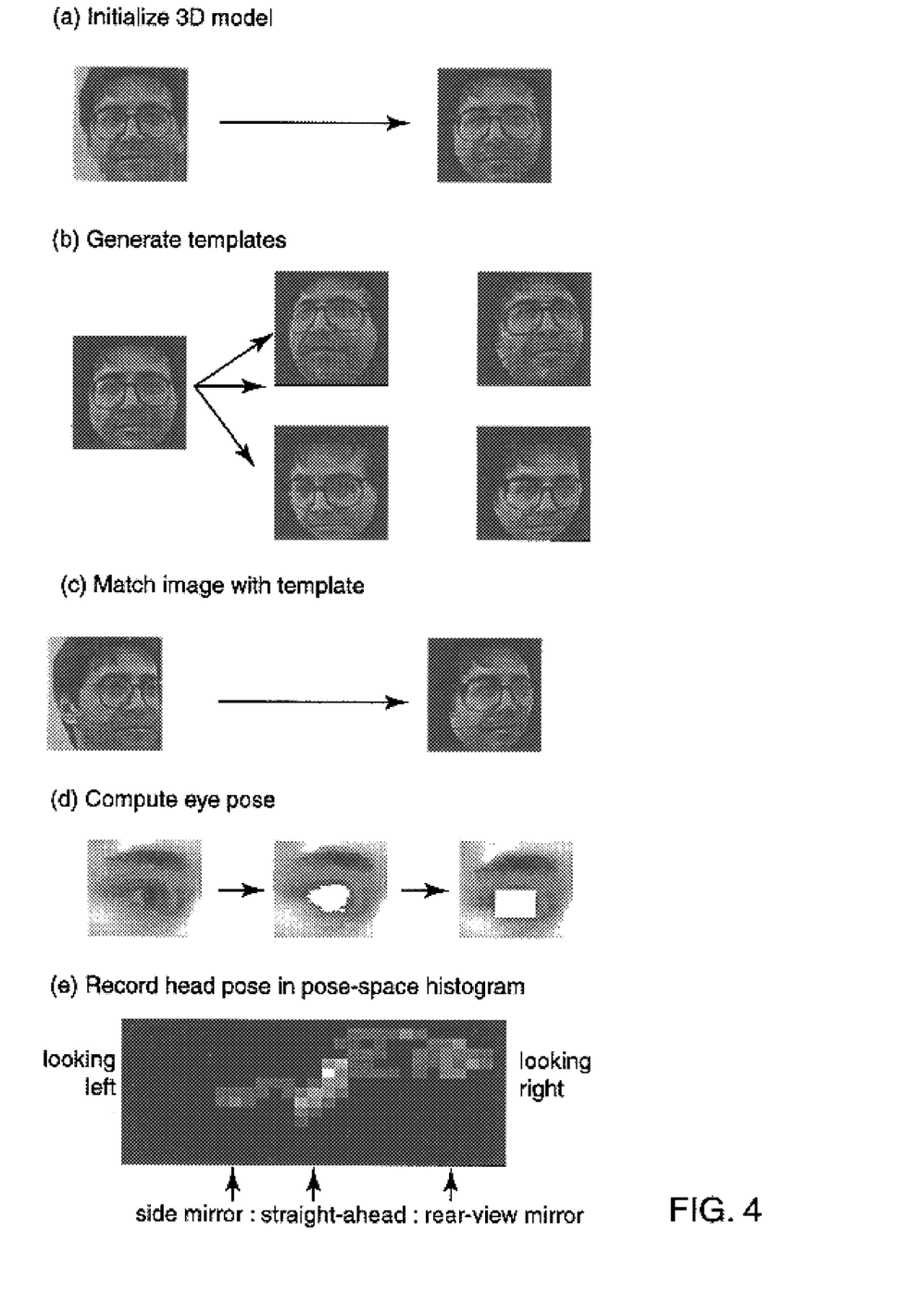
FIGS. 4A–E are a series of images describing initialization, template generation, image matching with a template, eye pose computation, and the recording of the head pose in a pose space histogram; in which an image of the individual is aligned with the generic head model; the templates are generated; an image of the individual is processed to determine the template most similar in appearance; the eye pose is processed; and the element in the pose-space histogram corresponding to the matched template is incremented, leading over time to the development of peaks in the pose-space histogram which indicate the most frequently adopted head poses of the individual.

More particularly as to processing head pose, as to initialization, initialization involves the creation of a 3D coordinate frame containing the camera and a 3D model of the head, consistent with the physical setup. FIG. 4A shows a reference image of the subject at left, which is cropped to the projection of the 3D model at right.

As to generating a template, once the coordinate frame containing the camera and the 3D model has been initialized, it is possible to generate a synthetic view of the face consistent with any specified rotation of the head. This is effectively done by backprojecting image texture from the reference image, as in FIG. 4B at left, onto the 3D model, and reprojecting using a camera at a different location, as in FIG. 4B at right In practice, the reprojection takes place directly between the images. As can be seen in FIG. 4C, images of a subject are matched with the most similar template.

Here an image is matched to the most similar template, namely that image shown to the right. The template is one which is formed as illustrated in FIG. 4B.

In order to further define the gaze direction, it is important to classify eye pose. As shown in FIG. 4D, the eye of the subject is segmented, and an "equivalent rectangle" is generated. This rectangle is useful in specifying whether the gaze direction is straight-ahead or downwards towards, for instance, an automobile dashboard.

As can be seen in FIG. 4E, the system records head pose in a pose-space histogram, recorded for an automobile driver. A bright spot to the left of the figure indicates the driver looked left. If the bright spot is not only left but is below the horizontal center line, one can deduce that the driver is looking at a lower side mirror. If the bright spot is in the center, then it can be deduced that the driver is looking straight-ahead. If the bright spot is upwards and to the right, one can deduce that the driver is looking upwardlt towards the rear-view mirror. In this manner, the pose-space histogram provides a probabilistic indication of the gaze direction of the driver without having to physically measure head position or eye direction.

Figure 5:
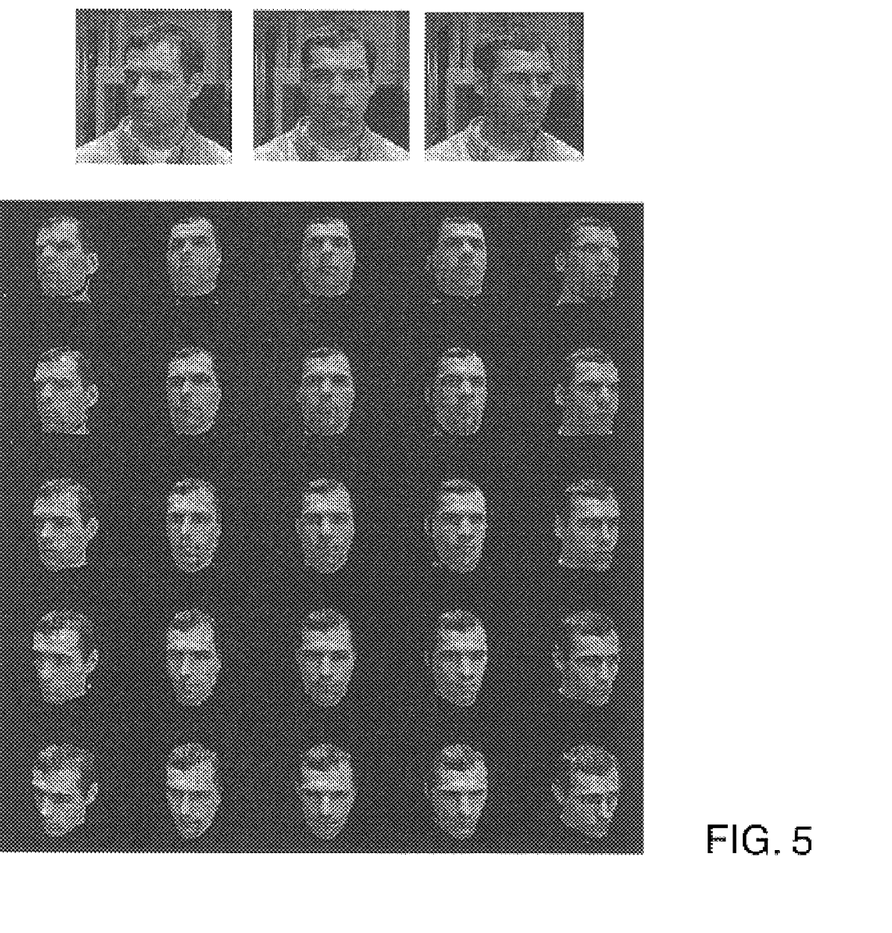
FIG. 5 is a series of acquired images of an individual, plus a small number of example templates from the full set of templates generated from the acquired images, with the templates showing different synthetically generated rotations of the head.

Referring now to FIG. 5, three images of a subject are used to generate a set of typically several hundred templates showing the subject from a variety of viewpoints. Some example templates are shown in FIG. 5 illustrating the subject looking right, towards the center, and left, both upwardly, straight-ahead, and downward. Two types of 3D model have been investigated—an ellipsoid as described in "Motion regularization for model-based head tracking" by S. Basu et al, 13th Int'l Conference on Pattern Recognition, Vienna, 1996, and a generic head model as described in "Head Pose Determination from One Image Using a Generic Model" by I. Shimizu et al, 3rd Intl Conf on Face and Gesture Recognition, 1998. A generic head model was used to generate the views in FIG. 5. The advantage of the ellipsoid model is that it allows quick initialization of many templates, of the order of seconds for 200 templates of 32×32 resolution, and minor misalignments of the ellipsoid with the reference image have little effect on the final result. The generic head model requires more careful alignment but it clearly gives more realistic results and this improves the quality of the processing which will be described subsequently. Some artifacts, visible in FIG. 5, occur because the generic head model is only an approximation to the actual shape of the subject's face.

Template generation is done offline at initialization time. It is carried out for a range of rotations, around the horizontal axis through the ears, and the vertical axis through the head, to generate an array of templates. Typically we use ±35° and ±60° around the horizontal axis and vertical axes respectively and generate an 11×17 array. The example in FIG. 5 shows a small selection of images taken from the full array. Cyclorotations of the head are currently ignored because these are relatively uncommon motions, and there is in any case some resilience in the processing to cyclorotation.

Figure 6:
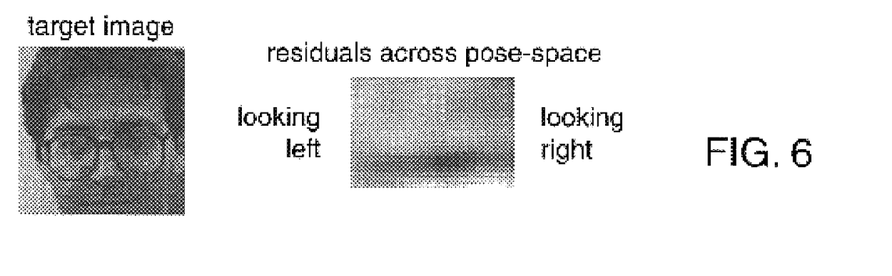
FIG. 6 is a typical acquired image together with the error surface generated by matching the image against each template, with darker areas indicating lower residuals and thus better matching, and with the error surface being well-behaved, with a clear minimum at the expected location.

FIG. 6 shows a typical target image together with the error surface generated by matching the target against each image in the array of templates. The error surface is often well-behaved, as shown here. The horizontal elongation of the minimum occurs because the dominant features in the matching process are the upper hairline, the eyes, and the mouth, all horizontally aligned features so that horizontal offsets have smaller effect on the matching score in equation (1) than vertical offsets.

Figure 7:
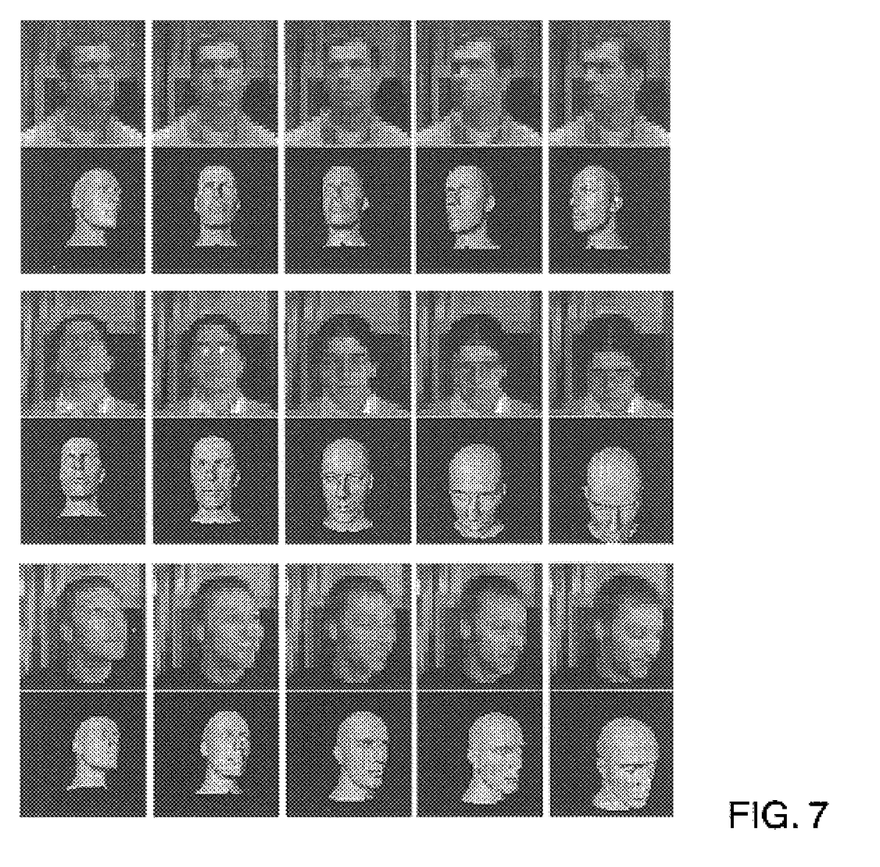
FIG. 7 is a series of image sequences for different subjects with the computed head motion, based on the matched template, shown by the 3D model beneath each image, also showing resilience to strong illumination gradients on the face, specularities on glasses, and changing facial expression.

FIG. 7 shows tracking for a number of different subjects. For each image, the best-matching template has been found, and a 3D head model is illustrated with pose given by the pose angles which were used to generate that template.

As to processing eye pose, work on processing eye pose has been targeted at one specific task, which is the discrimination of whether a car driver is looking straight forward or at the dashboard, since head pose alone is insufficient for this discrimination in most subjects. The approach is again qualitative, avoiding explicit computation of 3D euclidean rays for eye direction.

Figure 8:
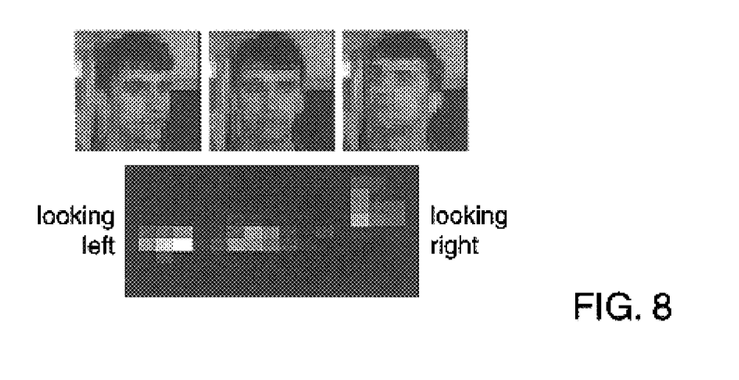
FIG. 8 is a series of images and corresponding pose-space histogram for three head poses adopted repeatedly over an extended sequence, with the histogram showing three distinct peaks as lightened areas.

FIG. 8 shows the result of an experiment in which the subject repeatedly views three different locations over an extended period, with a short pause at each location. The three locations correspond to the rear-view mirror, the side-mirror, and straight-ahead for a car driver. The pose-space histogram shows distinctive peaks for each location.

Figure 9:
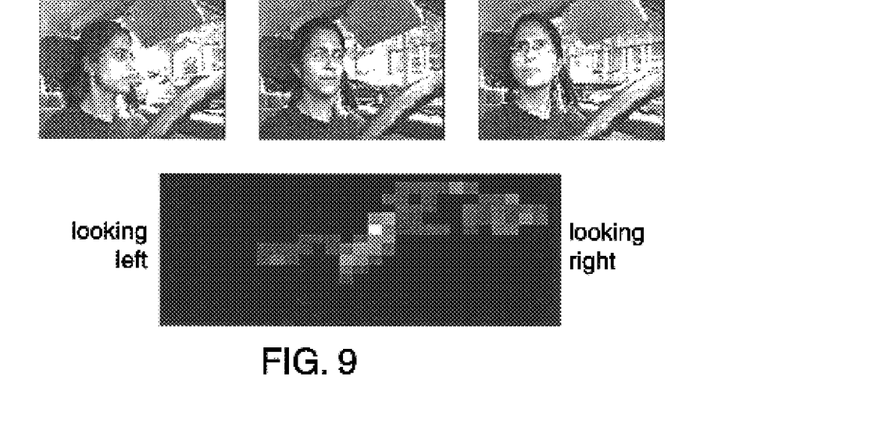
FIG. 9 is a series of images showing three samples from a driving sequence, with the corresponding pose-space histogram showing a peak as a lightened area for the driver looking straight-forward, and side lobes as slightly darker areas corresponding to the individual viewing the side and rear-view mirrors.

FIG. 9 shows the pose-space histogram for a short video sequence of a driver in a car. There is a peak for the straight-ahead viewing direction, and lobes to the left and right correspond to the driver looking at the side and rear-view mirrors.

Figure 10:
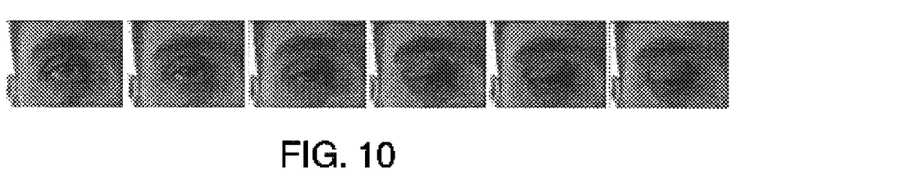
FIGS. 10 is a series of images showing how directing the gaze downward results in dropping of the eyelid which obscures a clear view of the iris and pupil, with the measurement of the dropping of the eyelid used to classify whether a driver is looking straight-forward or at the dashboard.

While active systems which use reflected infra-red are able to identify the location of the pupil very reliably, this is a more difficult measurement in a passive system, particularly when the gaze direction is directed downward. FIG. 10 shows how directing the gaze downward results in dropping of the eyelid, which obscures a clear view of the iris and pupil. The approach below uses the dropping of the eyelid to classify whether a driver is looking straight-forward or at the dashboard.

Figure 11:
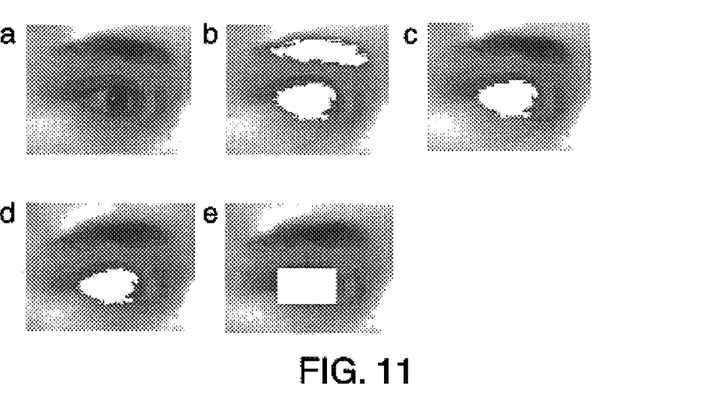
FIGS. 11A–E are images showing processing in the region of the eye, segmenting out non-skin areas, retaining the lower area, and replacing that area with an equivalent rectangle.

In FIG. 11, the current head pose is known at this stage, obtained via the processing in FIG. 2. Thus the approximate location of the eye is also known, and an algorithm to segment the eye is targetted to the appropriate part of the image, as shown in FIG. 11A. The segmentation in FIG. 11B and C is achieved using the Color Predicate scheme described in "Finding skin in color images" by R. Kjeldsen et al, 2nd Intl Conf on Automatic Face and Gesture Recognition, 1996. In this approach, training examples of skin and non-skin colors are used to label each element in a quantized color space. Kjeldsen found that the same Color Predicate could be used to segment skin in many human subjects. In this work so far a new Color Predicate is generated for each subject. In the first stage of segmentation, each pixel in the target area is labelled as skin or non-skin, regions of connected non-skin pixels are generated, and tiny non-skin regions, if any, are discarded. Typically two large non-skin regions are detected, for the eye and the eyebrow as shown in FIG. 11B. The eye is selected as the region which is physically lowest in the target area, FIG. 11C.

The warping in FIG. 11D is intended to generate the appearance of the eye for a face which is fronto-parallel to the camera, thus factoring out perspective effects. In the general case, this warping is derived from two pieces of information, the rotation of the head which makes the face fronto-parallel to the camera, known from the estimated head pose, and the 3D shape around the eye. To avoid the latter requirement, the area around the eye is assumed locally planar with normal equal to the forward direction of the face. The warping can then be expressed as a planar projectivity. This is straightforward to derive from the required head motion.

The equivalent rectangle of the segmented shape is shown in FIG. 11E. This representation was used in "Computer Vision for Interactive Computer Games" by Freeman et al, IEEE Computer Graphics and Applications, Vol 18, No 3, 1998, to analyze hand gestures. The segmented image is treated as a binary image, and the segmented shape is replaced with a rectangle which has the same moments up to second order. The ratio of height to width of the equivalent rectangle gives a measure of how much the eyelid has dropped. A fixed threshold is applied to this ratio to classify a driver's eye direction as forward or toward the dashboard. FIG. 12 shows an example of the narrowing of the segmented area as the eyelid drops.

Of course, the dropping of the eyelid occurs during blinking as well as for downward gaze direction. The two cases can be differentiated by utilizing the duration of the eye state, since blinking is transitory but attentive viewing has a longer timespan.

As to matching against templates, processing a target image of the driver involves comparing that image with each of the templates to find the best match, see FIG. 4C. A culling process is first carried out based on the shape signature e.g. 1D projection and moments, of the segmented skin area in the target image and templates, to eliminate templates which are clearly a poor match.

For the surviving templates, consider a target image I which is being matched against a template S. The goodness of match M between the two is found by computing $$M = \Sigma 1 - \cos(I_d(i,j) - S_d(i,j)) \qquad (1)$$

where $I_d(i,j)$, $S_d(i,j)$ are the directions of the gradient of the image intensity at pixel (i,j) in the target image and template respectively, and the summation is over all active pixels in the template. The best-matching template is the one which minimizes this score.

The target image is matched against a template for a range of offsets around the default position. Typically the range of offsets is ±4 pixels in steps of 2 pixels.

As to using multiple reference images, the basic scheme is extended to make use of three reference images of the subject in the following way. The fronto-parallel reference image is used to generate an array of templates. The subject looks to the left, a left-facing reference image is taken, and the best-match template is computed. All entries in the array which correspond to more extreme left-turn rotations than the best-match are now regenerated, using the left-facing reference image. This is repeated on the right side. This provides better quality templates for the more extreme rotations of the head.

As to the pose-space histogram, the algorithm for processing head pose does not deliver accurate measurements of head orientation because the head model is approximate and the computable poses are quantized. However, it does allow identification of frequently adopted head poses, together with the relative orientation of those poses, and that information provides the basis for classifying the driver's view direction.

Corresponding to the 2D array of templates of the head, a 2D histogram of the same dimensions is set up. All elements in the array are initialized to zero. For each new target image of the driver, once the best-matching template has been found, the corresponding element in the histogram is incremented. Over an extended period, peaks will appear in the histogram for those head poses which are being most frequently adopted.

Ideally, one would expect to find a peak corresponding to the driver looking straight-ahead, a peak to the left of this for viewing the left-side mirror, and a peak to the right for viewing the rear-view mirror as illustrated in FIG. 4E. Observed peaks can be labelled automatically in accordance with this. Thereafter, for any acquired image of the driver, the best-matching template is found, the corresponding location in the histogram is indexed, and the target image is classified according to its proximity to a labelled peak. In this way, classification of the driver's focus of attention is achieved without any quantitative information about the 3D layout of the car.

As to results, some experiments were carried out on 32×32 images captured by the Artificial Retina of the Mitsubishi Electric Company. Others were carried out on 192×192 images captured by a Sony Hi-8 video camera. The processing speed is about 10 Hz for computing head pose with 32×32 images on an SGI workstation.

Since the main idea of the subject system is to avoid explicit measurement of the rotation angles of the head, no quantitative measurements about head pose are given, but various aspects of the performance of the system are illustrated.

Having now described a few embodiments of the invention, and some modifications and variations thereto, it should be apparent to those skilled in the art that the foregoing is merely illustrative and not limiting, having been presented by the way of example only. Numerous modifications and other embodiments are within the scope of one of ordinary skill in the art and are contemplated as falling within the scope of the invention as limited only by the appended claims and equivalence thereto.

What is claimed is:

1. A system to classify the gaze direction of an individual observing a number of surrounding objects, comprising:

means for observing the head pose of an individual;

means for generating a number of templates corresponding to different gaze directions of said individual as said individual looks in different gaze directions;

means for matching an image of said individual with the template which is most similar in appearance;

means utilizing said matched templates for generating a pose-space histogram recording the frequency of different head poses over a predetermined period of time, said histogram recording as peaks over time frequently viewed directions towards said number of surrounding objects, with each peak labelled utilizing a qualitative description of the environment around said individual;

means coupled to said head pose observing means and said pose-space histogram for determining that peak which most closely corresponds to the current gaze direction of said individual, whereby gaze direction is classified without direct measurement of head position or eye direction.

2. The system of claim 1 and further including means for augmenting said classification to permit more rapid classification of gaze including means for establishing eye pose.

3. The system of claim 2, wherein said means for establishing eye pose includes means for determining eyelid droop.

4. The system of claim 3, wherein said means for determining eyelid droop includes means for identifying the area in the image occupied by the eye using color, means for classifying the shape of the segmented eye using an equivalent rectangle and, means for determining the ratio of the height of said rectangle to the width thereof, whereby said ratio determines eyelid droop and thus whether the eye is looking straight-ahead or in a downward direction.

5. The system of claim 1 wherein said means for matching images with a template includes cross-correlation of an image of said individual with all of said templates in order to identify the most similar template.

6. The system of claim 1 and further including means for storing said templates during an initialization phase such that said templates are available during subsequent real-time classification, thereby eliminating time-consuming template generation during classification.

7. The system of claim 1 and further including means for culling out templates which are a poor match for the image of said individual.

8. The system of claim 7 wherein said culling means includes means for segmenting the skin portion of said image using color to provide a unique shape signature corresponding to said segmented skin area made available by said color segmentation, means for generating shape signatures for each of said templates, means for matching the shape signature of said image with shape signatures of said templates and means for eliminating from consideration those templates having shape signatures exhibiting poor correspondence.

9. The system of claim 8 wherein said means for segmenting the skin portion of said image using color to provide a unique shape signature corresponding to said segmented skin area includes means for generating 1D projections and moments of segmented skin areas, thus to provide said signature.

* * * * *